(12) United States Patent
Smith et al.

(10) Patent No.: US 8,845,693 B2
(45) Date of Patent: Sep. 30, 2014

(54) TULIP HEAD APPARATUS

(76) Inventors: Jeffrey Scott Smith, Granbury, TX (US); Soojung Moon, Kissimmee, FL (US)

(*) Notice: Subject to any disclaimer, the term of this patent is extended or adjusted under 35 U.S.C. 154(b) by 58 days.

(21) Appl. No.: 13/401,339

(22) Filed: Feb. 21, 2012

(65) Prior Publication Data

US 2012/0277806 A1 Nov. 1, 2012

Related U.S. Application Data (60) Provisional application No. 61/479,396, filed on Apr. 27, 2011.

(51) Int. Cl.
*A61B 17/70* (2006.01)
(52) U.S. Cl.
CPC ......... *A61B 17/7032* (2013.01); *A61B 17/7035* (2013.01)
USPC ........................................... 606/270; 606/268
(58) Field of Classification Search
USPC .......................... 606/246, 250–275, 300–321
See application file for complete search history.

(56) References Cited

U.S. PATENT DOCUMENTS

| 6,248,105 | B1 | 6/2001 | Schlapfer | |
|---|---|---|---|---|
| 6,280,442 | B1 | 8/2001 | Barker | |
| 6,302,888 | B1 | 10/2001 | Mellinger | |
| 6,440,137 | B1 | 8/2002 | Horvath | |
| 6,443,953 | B1 | 9/2002 | Perra | |
| 6,565,567 | B1 | 5/2003 | Haider | |
| 6,755,829 | B1 | 6/2004 | Bono | |
| 7,186,255 | B2 | 3/2007 | Baynam | |
| 7,294,128 | B2 | 11/2007 | Alleyne | |
| 7,691,129 | B2 | 4/2010 | Felix | |
| 7,871,413 | B2 | 1/2011 | Park | |
| 7,967,850 | B2 | 6/2011 | Jackson | |
| 8,016,862 | B2 | 9/2011 | Felix et al. | |
| 8,016,866 | B2 | 9/2011 | Warnick | |
| 8,197,517 | B1* | 6/2012 | Lab et al. | ........................ 606/268 |
| 2006/0089644 | A1* | 4/2006 | Felix | ................................ 606/61 |
| 2007/0288004 | A1* | 12/2007 | Alvarez | ............................. 606/61 |
| 2009/0036934 | A1 | 2/2009 | Biedermann | |
| 2009/0198280 | A1 | 8/2009 | Spratt | |

* cited by examiner

*Primary Examiner* — Matthew Lawson
(74) *Attorney, Agent, or Firm* — Workman Nydegger (57) ABSTRACT

A tulip head apparatus includes a chuck housing configured to join to a head of a screw. The chuck housing comprises an upward slot extending from a bottom for enabling the chuck housing to expand to enable entry of the head and to contract to retain the head. A plurality of downward slots extends from a top for enabling a portion of the chuck housing to contract and expand. A plurality of hook structures are disposed about the top. A rotating head includes a hollow portion having a circular groove and to accept the chuck housing in which a contraction of the portion enables entry of the chuck housing and expansion of the portion engages the hook structures with the groove to secure the chuck housing within the rotating head and enable the rotating head to rotate about the chuck housing.

11 Claims, 5 Drawing Sheets

TULIP HEAD APPARATUS

CROSS-REFERENCE TO RELATED APPLICATIONS

The present Utility patent application claims priority benefit of the U.S. provisional application for patent Ser. No. 61/479,396 entitled "Top Loading Pedicle Screw Assembly", filed on Apr. 27, 2011 under 35 U.S.C. 119(e). The contents of this related provisional application are incorporated herein by reference for all purposes to the extent that such subject matter is not inconsistent herewith or limiting hereof.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to medical devices. More particularly, one or more embodiments of the invention relate to a pedicle screw assembly with a rotating head that may be attached to the top of the screw without passing the screw through the rotating head.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Occasionally, pedicle screws are used to assist in the fixation of bones in spine surgeries such as, but not limited to, spinal fusions. Pedicle screws generally comprise a straight threaded screw with a rounded head. The rounded head is typically attached to a piece, commonly referred to as a tulip head, which can be rotated and can accept a rod for fixation.

By way of educational background, an aspect of the prior art generally useful to be aware of is that currently known pedicle screws are generally passed through the tulip head for insertion. In addition, surgeons often wish to keep the tulip head profile as small as practical. One can expect that the common requirement of passing the screw through the tulip head for assembly and the common desire to use a tulip head with a small profile may result in limiting the diameter of the screw as the screw diameter generally cannot exceed the size of the tulip head.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 1A through 1C illustrate an exemplary screw assembly with a rotating head, in accordance with an embodiment of the present invention.

FIGS. 6A through 6C illustrate an exemplary locking chuck that may be attached to a screw through a side slot, in accordance with an embodiment of the present invention.

Unless otherwise indicated illustrations in the figures are not necessarily drawn to scale.

DETAILED DESCRIPTION OF SOME EMBODIMENTS

Embodiments of the present invention are best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

One or more embodiments of the present invention may apply to a system for attaching a rotating tulip head to a fixed screw head. Some embodiments may be implemented for use with pedicle screws that are often used in spine surgery. Other embodiments may be used for various different applications in which an item is to be attached to a screw head. Traditional pedicle screws are generally limited in the size of their threaded diameter because the screw typically must be passed through the tulip head for insertion. The common need in many surgical procedures of the spine to keep the tulip head profile small generally makes the use of larger diameter screws impractical.

Figure 1A:
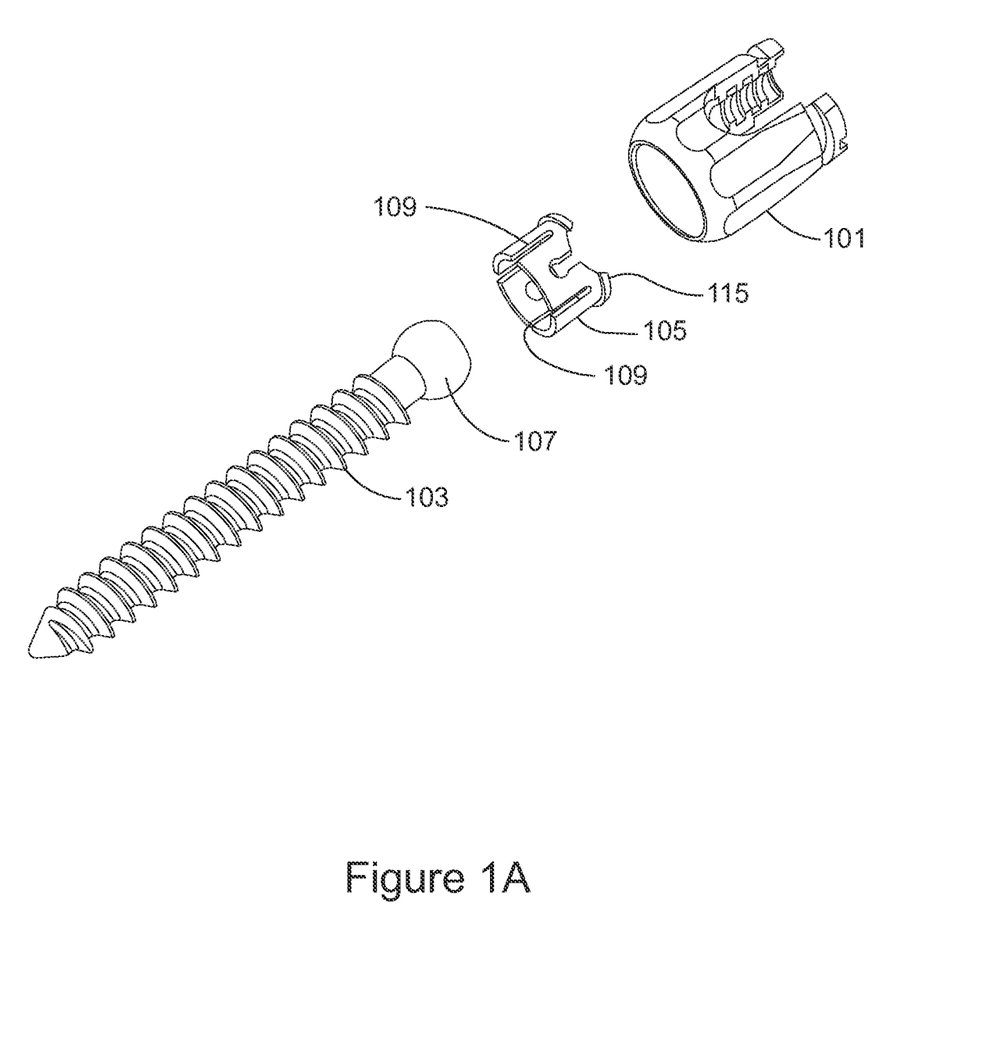
FIG. 1A is an exploded side perspective view of the screw assembly.
Figure 1B:
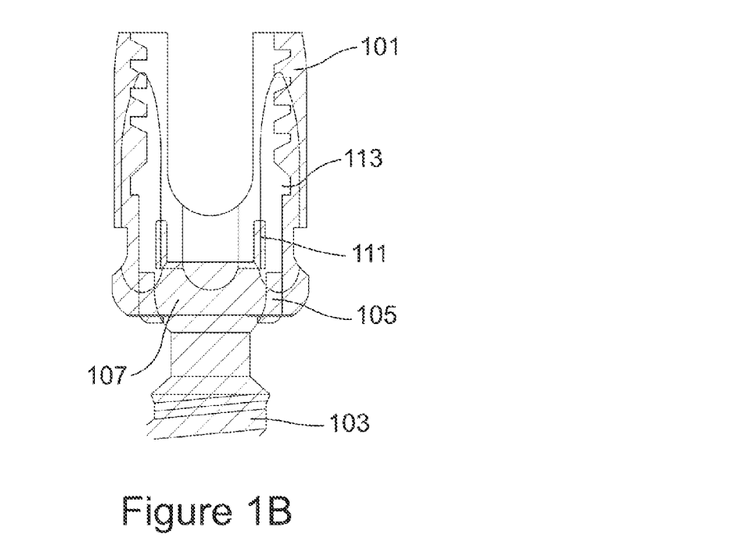
FIG. 1B is a cross sectional view of a head section of the screw assembly.
Figure 1C:
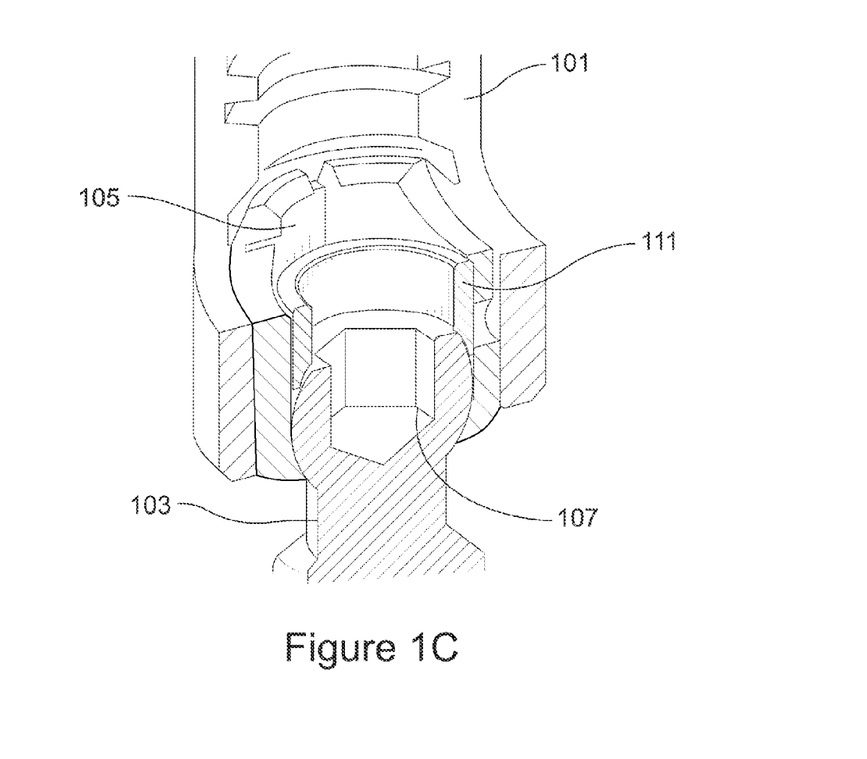
FIG. 1C is a partially cut away side perspective view of the head section of the screw assembly.

FIGS. 1A through 1C illustrate an exemplary screw assembly with a rotating head 101, in accordance with an embodiment of the present invention. FIG. 1A is an exploded side perspective view of the screw assembly. FIG. 1B is a cross sectional view of a head section of the screw assembly, and FIG. 1C is a partially cut away side perspective view of the head section of the screw assembly. In the present embodiment, the design of the screw assembly generally enables rotating head 101 to be attached to a fixed pedicle rounded head 107 of a screw 103 without passing screw 103 through rotating head 101. Rotating head 101 may be attached to the top of screw 103 through a snap together technique. Rounded head 107 of pedicle screw 103 accepts a locking chuck 105, which snaps over rounded head 107. This is made possible by locking slots 109 on locking chuck 105 which enable chuck 105 to expand as it is passed over rounded head 107 and then retract back together to lock chuck 105 in place on rounded head 107. Chuck 105 then accepts rotating head 101 from the opposite direction utilizing a similar expanding and retracting mechanism.

Referring to FIGS. 1B and 1C, an inner locking ring 111 helps secure the assembled screw assembly to a connecting rod, which can be used to attach screw 103 to a bone or other item, etc. Additional screw assemblies may also be attached to the connecting rod Inner ring 111 supports locking chuck 105 and holds rotating head 101 in place with additional support from compressive loads provided by the positioning of a connection rod within rotating head 101. Some alternate embodiments may be implemented without an inner locking ring. In the present embodiment, a groove 113 in rotating head 101 accepts locking hooks 115 of locking chuck 105 to hold rotating head 101 and locking chuck 105 together. Groove 113 encircles the inner surface of rotating head 101. Locking hooks 115 are typically able to slide within groove 113 to generally enable rotating head 101 to rotate 360 degrees on screw 103. Rounded head 107 of screw 103 is generally held in place by the inside walls of locking chuck 105 and rotating head 101. In the present embodiment, the elements of the screw assembly can be made from various different biocompatible materials with sufficient strength and elasticity for function, such as, but not limited to, stainless steel, titanium or carbon fiber. The elasticity of the chosen material generally enables motion to occur particularly at the slotted areas of chuck 105 to allow for assembly from the top of screw 103. It is contemplated that some alternate embodiments for use in various different applications may be made of non-biocompatible materials including, without limitation, different types of metals or various different plastics.

In the present embodiment, rotating head 101 can be attached to fixed rounded head 107 of screw 103 without passing screw 103 through rotating head 101. The diameter of the screw used is typically not restrained by the size of rotating head 101. Locking chuck 105 generally fits within rotating head 101 and typically does not add to the profile of the complete screw assembly.

Figure 2:
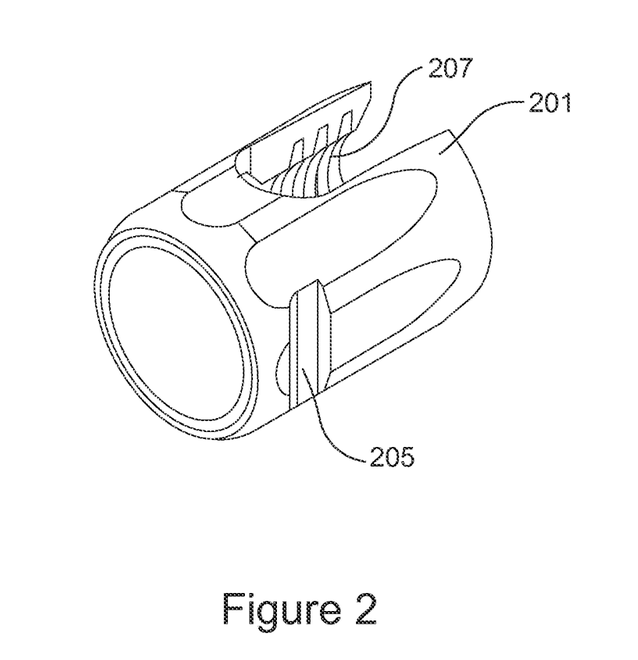
FIG. 2 is a side perspective view of an exemplary rotating head from a screw assembly, in accordance with an embodiment of the present invention.

FIG. 2 is a side perspective view of an exemplary rotating head from a screw assembly, in accordance with an embodiment of the present invention. In the present embodiment, the rotating head comprises a housing 201 configured to prevent the spreading of the rotating head during tightening. Housing 201 also comprises a holding groove 205 on each side. Holding grooves may be used to grab housing 201 with an instrument. It is contemplated that some alternate embodiments may be implemented without holding grooves. In the present embodiment, threads 207 inside the rotating head enable threaded objects such as but not limited to, connection rods to be attached to the rotating head. In some alternate embodiments the rotating head may comprise a multiplicity of suitable connection means and inner surfaces such as, but not limited to, sockets of various different shapes to accept various different types of rods, smooth surfaces, knurled surfaces, etc. In the present embodiment, the rotating head may be similar in size and shape to standard rotating screw heads. Those skilled in the art will readily recognize, in light of and in accordance with the teachings of the present invention, that rotating heads in some alternate embodiments may be made in non-standard sizes and shapes.

Figure 3:
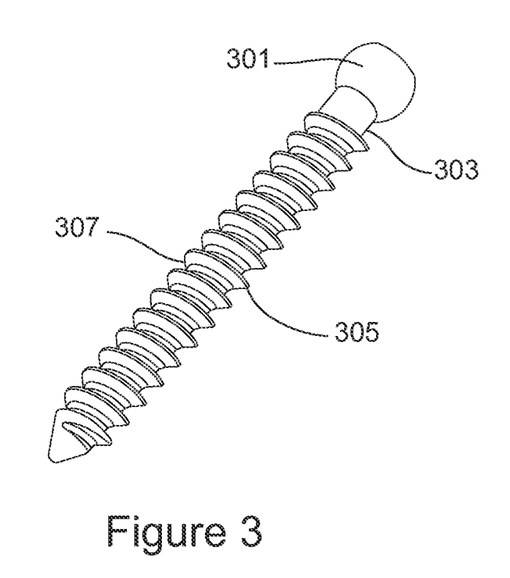
FIG. 3 is a side perspective view of an exemplary screw from a screw assembly, in accordance with an embodiment of the present invention.

FIG. 3 is a side perspective view of an exemplary screw from a screw assembly, in accordance with an embodiment of the present invention. In the present embodiment, the screw comprises a rounded head 301, which may be connected to a locking chuck, as shown by way of example in FIGS. 1A and B. The screw also comprises a thread neck 303, and threads 305 on a double tapered core 307. Those skilled in the art will readily recognize, in light of and in accordance with the teachings of the present invention, that various different types of threads and cores may be used in some alternate embodiments including without limitation bolt threads or a smooth pin. Furthermore, some alternate embodiments may have heads of various different shapes such as, but not limited to, cylindrical heads, cubical heads, conical heads, etc.

Figure 4:
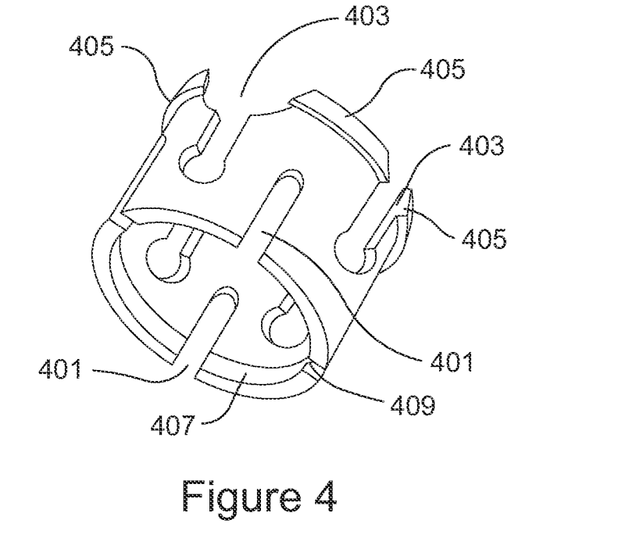
FIG. 4 is a side perspective view of an exemplary locking chuck from a screw assembly, in accordance with an embodiment of the present invention.

FIG. 4 is a side perspective view of an exemplary locking chuck from a screw assembly, in accordance with an embodiment of the present invention. In the present embodiment, the locking chuck enables a rotating head to be attached securely to the head of a pedicle screw. The locking chuck comprises lower locking slots 401 that allow the chuck to expand and contract to allow snap on assembly with the head of a pedicle screw. The locking chuck also comprises upper locking slots 403 that enable the locking chuck to compress to when a rotating head is slid over the locking chuck and then expand to lock the rotating head in place. It is contemplated that some alternate embodiments may be implemented locking slots in a multiplicity of suitable numbers and configurations. For example, without limitation, one alternate embodiment may comprise two lower locking slots on opposite sides of the chuck and two upper locking slots on opposite sides of the chuck positioned perpendicularly to the lower locking slots. In the present embodiment, locking hooks 405 fit into a groove in the rotating head, as shown by way of example in FIGS. 1A and 1B, to hold the rotating head in place on the locking chuck after assembly. In some alternate embodiments, the locking hooks may be located on the rotating head to hook into a groove on the locking chuck. It is contemplated that other alternate embodiments may incorporate a multiplicity of suitable alternate means for locking the locking chuck to the rotating head such as, but not limited to, nubs or pins that snap into grooves, threaded attachment means, etc. Yet other alternate embodiments may be implemented in which the locking chuck is permanently attached to the rotating head. In the present embodiment, a motion groove 407 at the bottom of the locking chuck where the chuck contacts the screw typically holds the chuck on the head of the screw. Moreover, motion groove 407 generally provides increased angular motion with the rounded head of the screw. In some alternate embodiments, the locking chuck may not comprise a motion groove. In the present embodiment, a small lip 409 above motion groove 407 assists in holding the locking chuck on the screw head.

Figure 5:
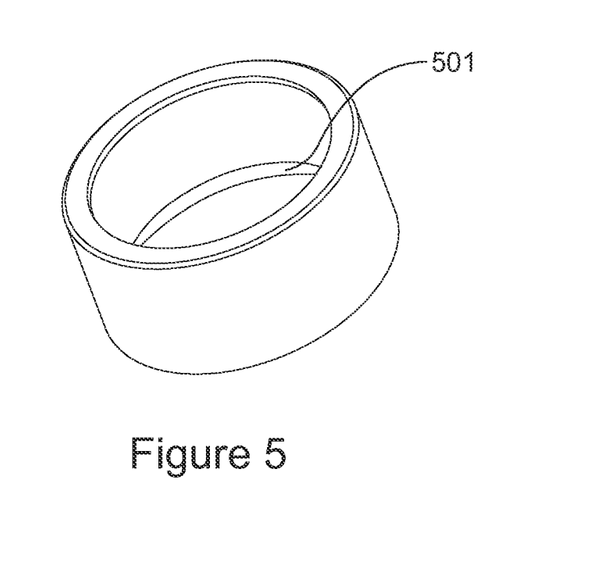
FIG. 5 is a side perspective view of an exemplary inner locking ring from a screw assembly, in accordance with an embodiment of the present invention.

FIG. 5 is a side perspective view of an exemplary inner locking ring from a screw assembly, in accordance with an embodiment of the present invention. In the present embodiment, the inner locking ring is a substantially cylindrical ring that fits within the locking chuck and rests upon the rounded head of a pedicle screw. The lower surface of the locking ring comprises an angled inner edge 501 that enables the locking ring to partially fit over the rounded head of the screw. The inner ring supports the assembly and holds the screw head tightly after rod assembly. Some alternate embodiments may be implemented without an inner locking ring.

Figures 6A, 6B, 6C:
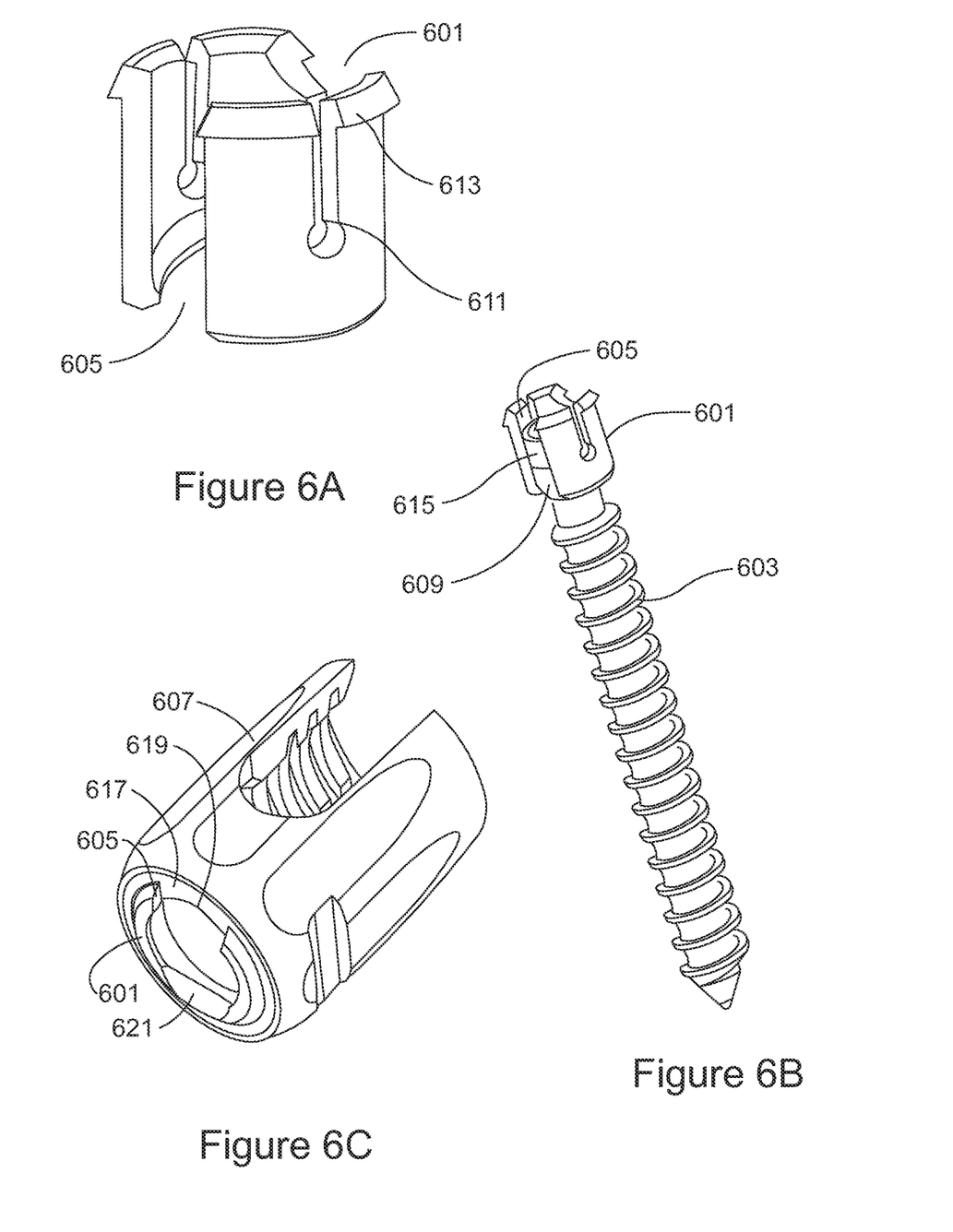
FIG. 6A is a side perspective view of the locking chuck.
FIG. 6B is a side perspective view of the locking chuck on the screw.
FIG. 6C is a side perspective view of the locking chuck inserted into a rotating head.

FIGS. 6A through 6C illustrate an exemplary locking chuck 601 that may be attached to a screw 603 through a side slot 605, in accordance with an embodiment of the present invention. FIG. 6A is a side perspective view of locking chuck 601. FIG. 6B is a side perspective view of locking chuck 601 on screw 603, and FIG. 6C is a side perspective view of locking chuck 601 inserted into a rotating head 607. In the present embodiment, locking chuck 601 can be attached to a screw head 609 from the side through side slot 605, which may be a full length opening in chuck 601 that typically enables chuck 601 to expand so that chuck 601 can pass over screw head 609. Slot 605 then comes back together after chuck 601 is snapped onto screw head 609. Then rotating head 607 may be snapped over chuck 601. In some alternate embodiments, the side slot may be located along a portion of the side of the locking chuck rather than being a full length opening. Referring to FIG. 6A in the present embodiment, upper locking slots 611 enable rotating head 607 to easily snap onto chuck 601, and locking hooks 613 hook into a groove in rotating head 607 to hold chuck 601 in rotating head 607. Referring to FIG. 6B, an inner locking ring 615 is shown in place inside chuck 601 and on top of screw head 609. Referring to FIG. 6C, a bump 617 is located at the bottom portion of rotating head 607, near where rotating head 607 contacts the neck of screw 603. Bump 617 acts as a guide during assembly since bump 617 fits within side slot 605 in locking chuck 601. Bump 617 comprises an arc 619 to generally optimize head angulation. Furthermore, chuck 601 also comprises a motion groove 621 at the area of contact with screw 603, which can increase the angle of screw rotation.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods of providing a pedicle screw assembly according to the present invention will be apparent to those skilled in the art. The invention has been described above by way of illustration, and the specific embodiments disclosed are not intended to limit the invention to the particular forms disclosed. For example, the particular implementation of the locking chuck may vary depending upon the particular type of attachment mechanism used. The attachment mechanisms described in the foregoing were directed to locking slot implementations; however, similar techniques are to provide locking chucks that may be attached to screw heads and rotating heads using various different means such as, but not limited to, specially shaped holes, set screws, threaded attachment means, etc. For example, without limitation, in one alternate embodiment the locking chuck may comprise a hole on the side which is generally sized and shaped to accept a screw head and a collar or sliding mechanism to cover a portion of or the entire hole once the screw head is inserted to hold the screw head in place. Implementations of the present invention utilizing attachment means other than locking slots are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A tulip head apparatus comprising:
   (a) a chuck housing being configured to join to a rounded head of a screw device, said chuck housing comprising:
   a generally cylindrical shape having a wall, a top and a bottom;
   a side slot through said wall and extending through said bottom and said top for enabling said chuck housing to expand to enable entry of the rounded head through said wall and to contract to retain the rounded head;
   a plurality of downward slots extending from said top for enabling a portion of said chuck housing to contract and to expand;
   a plurality of hook structures being disposed about said top; and
   a lip near the bottom of said chuck configured to contact a lower portion of the rounded head for retaining the rounded head within said chuck;
   (b) a rotating head being configured to join to said chuck housing, said rotating head comprising:
   a generally cylindrical shape having a wall, a top and a bottom;
   a hollow portion extending from said bottom;
   a circular groove being disposed on an inner surface of said wall;
   a bump portion that extends substantially longitudinally within the interior of and integral with said head, said bump portion enabling alignment with said side slot and inhibiting rotation of said head about said chuck said rotating head being configured to accept said chuck housing in which a contraction of said chuck housing enables entry of said chuck housing into said head and expansion of said chuck housing engages said hook structures into said groove to secure said chuck housing within said rotating head; and enable said rotating head to rotate about said screw head;
   (c) a locking ring being configured to fit inside said rotating head and engage said rounded head, said locking ring comprising a substantially cylindrical ring structure and with a bottom edge that enables said locking ring to partially fit over the rounded head of said screw device and retain said rounded head in a position; and
   (d) connection means being operable for securing at least a rod to said rotating head.

2. The tulip head apparatus as recited in claim 1, in which said bottom of said chuck housing further comprises a circular motion groove for increasing angular motion with respect to the rounded head.

3. The tulip head apparatus as recited in claim 1, in which said locking ring further comprises a beveled edge for contacting the rounded head.

4. The tulip head apparatus as recited in claim 1, in which said rotating head further comprises holding grooves for grasping the rotating head.

5. The tulip head apparatus as recited in claim 1, in which said connection means is further operable for securing a threaded object.

6. The tulip head apparatus as recited in claim 1, in which the screw device is a pedicle screw.

7. The tulip head apparatus as recited in claim 1, in which entry of the rounded head and said chuck housing are further enabled through said bottom of the rotating head.

8. The tulip head apparatus as recited in claim 7, in which said chuck housing further comprises a plurality of upward slots extending to positions below said top.

9. A tulip head apparatus comprising:
   (a) a chuck housing being configured to join to a rounded head of a screw device, said chuck housing comprising:
   a generally cylindrical shape having a wall, a top and a bottom, said bottom of said chuck housing comprising a circular motion groove for increasing angular motion with respect to the rounded head;
   a side slot extending through said bottom and said top for enabling said chuck housing to expand to enable entry of the rounded head through said wall and to contract to retain the rounded head;
   a lip disposed above said motion groove to contact a lower portion of the rounded head for further retaining the rounded head;
   a plurality of downward slots extending from said top for enabling a portion of said chuck housing to contract and to expand;
   a plurality of hook structures being disposed about said top;
   (b) a rotating head being configured to join to said chuck housing, said rotating head comprising:
   a generally cylindrical shape having a wall, a top and a bottom; a hollow portion extending from said bottom;
   a circular groove being disposed on an inner surface of said wall of the rotating head,
   said rotating head being configured to accept said chuck housing in which a contraction of said chuck housing portion enables entry of said chuck housing into said head and expansion of said chuck housing portion engages said hook structures into said groove to secure said chuck housing within said rotating head and enable said rotating head to rotate about said screw head;

said rotating head further comprising a bump portion that extends substantially longitudinally within the interior of and integral with said head, said bump portion enabling alignment with said side slot of said housing and inhibiting rotation of said head about said chuck;

(c) holding grooves for grasping the rotating head;

(d) connection means being operable for securing at least a threaded rod to said rotating head; and (e) a locking ring being configured to fit within said chuck housing said locking ring comprising a beveled edge for contacting the rounded edge and for retaining said rounded rotating head in a position.

10. The tulip head apparatus as recited in claim 9, in which entry of the rounded head into said chuck housing is further enabled through said bottom.

11. The tulip head apparatus as recited in claim 9, in which the screw device is a pedicle screw.

\* \* \* \* \*